(12) United States Patent
Kumar et al.

(10) Patent No.: US 9,931,470 B2
(45) Date of Patent: Apr. 3, 2018

(54) SELECTABLE SINGLE DOSE AUTO-INJECTOR AND METHODS OF MAKING AND USING SAME

(71) Applicant: Dr. Reddy's Laboratories Ltd., Hyderabad (IN)

(72) Inventors: Rajesh Kumar, Skillman, NJ (US); Anil Namboodiripad, Yardley, PA (US)

(73) Assignee: Dr. Reddy's Laboratories Ltd. (IN)

( * ) Notice: Subject to any disclaimer, the term of this patent is extended or adjusted under 35 U.S.C. 154(b) by 0 days.

(21) Appl. No.: 14/847,790

(22) Filed: Sep. 8, 2015

(65) Prior Publication Data

US 2015/0374918 A1 Dec. 31, 2015

Related U.S. Application Data

(63) Continuation of application No. 14/462,116, filed on Aug. 18, 2014.

(Continued)

(51) Int. Cl.
*A61M 5/315* (2006.01)
*A61M 5/20* (2006.01)
(Continued)

(52) U.S. Cl.
CPC ...... *A61M 5/2033* (2013.01); *A61M 5/31548* (2013.01); *A61M 5/31591* (2013.01);
(Continued)

(58) Field of Classification Search
CPC ............ A61M 5/2033; A61M 5/31548; A61M 5/31553; A61M 5/31591
See application file for complete search history.

(56) References Cited

U.S. PATENT DOCUMENTS 5,244,465 A * 9/1993 Michel ............... A61M 5/24
604/187
6,837,876 B2 1/2005 Bally et al.
(Continued)

FOREIGN PATENT DOCUMENTS

EP 1414506 A2 5/2004
EP 1742698 A2 1/2007
(Continued)

OTHER PUBLICATIONS

Imitrex Package Insert, GlaxoSmithKline, Jan. 2006.*
International Search Report and Written Opinion for Application No. PCT/US2014/051531 dated Oct. 24, 2014.

*Primary Examiner* — Theodore Stigell
*Assistant Examiner* — Benjamin Koo
(74) *Attorney, Agent, or Firm* — Lerner, David, Littenberg, Krumholz & Mentlik, LLP

(57) ABSTRACT

An auto-injector device for administering a liquid pharmaceutical composition, in which an end-user can select between doses that the device is capable of delivering. The end-user choices that translate into the selected doses can be based on end-user perceived severity of symptoms, end-user weight and other such factors. In some embodiments the auto-injector is configured to administer the one chosen dose only. In other embodiments, the auto-injector can deliver second and subsequent doses up to full dose of the pharmaceutical composition disposed in the injector. The auto-injector can provide visual, audio, and tactile feedback, alone or in combination, to the user to indicate the dose selected, instructions for use, and when the dose has been administered.

14 Claims, 7 Drawing Sheets

Related U.S. Application Data

(60) Provisional application No. 61/901,721, filed on Nov. 8, 2013, provisional application No. 61/867,349, filed on Aug. 19, 2013.

(51) Int. Cl.
*A61M 5/50* (2006.01)
*A61M 5/31* (2006.01)
*A61M 5/32* (2006.01)

(52) U.S. Cl.
CPC ............ *A61M 5/50* (2013.01); *A61M 5/3129* (2013.01); *A61M 5/3156* (2013.01); *A61M 5/31546* (2013.01); *A61M 5/31553* (2013.01); *A61M 5/31555* (2013.01); *A61M 5/321* (2013.01); *A61M 2005/206* (2013.01); *A61M 2005/208* (2013.01); *A61M 2005/2073* (2013.01); *A61M 2005/3126* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 6,859,673 B2 | 2/2005 | Steffen | |
| 6,972,007 B2 | 12/2005 | Geiser et al. | |
| 7,125,395 B2 | 10/2006 | Hommann et al. | |
| 7,169,131 B2 | 1/2007 | Gatti et al. | |
| 7,169,133 B2 | 1/2007 | Broennimann et al. | |
| 7,182,739 B2 | 2/2007 | Kopanic et al. | |
| 7,201,741 B2 | 4/2007 | Maire | |
| 7,214,213 B2 | 5/2007 | Michel et al. | |
| 7,377,913 B2 | 5/2008 | Gurtner | |
| 7,407,492 B2 | 8/2008 | Gurtner | |
| 7,511,480 B2 | 3/2009 | Steffen | |
| 7,727,201 B2 | 6/2010 | Kirchhofer | |
| 7,749,186 B2 | 7/2010 | Kohlbrenner et al. | |
| 7,758,550 B2 | 7/2010 | Bollenbach et al. | |
| 7,951,113 B2 | 5/2011 | Kohlbrenner et al. | |
| 7,976,509 B2 | 7/2011 | Moser et al. | |
| 8,038,655 B2 | 10/2011 | Burren et al. | |
| 8,048,037 B2 | 11/2011 | Kohlbrenner et al. | |
| 8,128,604 B2 | 3/2012 | Yeandel et al. | |
| 8,246,577 B2 | 8/2012 | Schrul et al. | |
| 8,500,701 B2 | 8/2013 | Kirchhofer | |
| 8,721,601 B2 | 5/2014 | Burren et al. | |
| 2003/0196929 A1* | 10/2003 | Gopinathan | A61J 1/00 206/570 |
| 2005/0245594 A1* | 11/2005 | Sutter | A61K 31/405 514/419 |
| 2006/0270985 A1 | 11/2006 | Hommann et al. | |
| 2010/0010454 A1* | 1/2010 | Marshall | A61M 5/2033 604/208 |
| 2013/0204229 A1 | 8/2013 | Olson et al. | |

FOREIGN PATENT DOCUMENTS

| | | | |
|---|---|---|---|
| EP | 1855740 A1 | 11/2007 | |
| WO | WO 01/41749 * | 6/2001 | ............ A61K 31/00 |
| WO | WO-2004007001 A1 | 1/2004 | |
| WO | WO-2004057959 A2 | 7/2004 | |
| WO | WO-2005035028 A1 | 4/2005 | |
| WO | WO-2005102421 A1 | 11/2005 | |
| WO | WO-2006057604 A1 | 6/2006 | |
| WO | WO-2009000095 A2 | 12/2008 | |
| WO | WO-2009141005 A1 | 11/2009 | |
| WO | WO-2010149466 A2 | 12/2010 | |
| WO | WO-2011088894 A1 | 7/2011 | |
| WO | WO-2012032411 A2 | 3/2012 | |
| WO | WO-2013170392 A1 | 11/2013 | |

\* cited by examiner

FIG. 7A
FIG. 7B
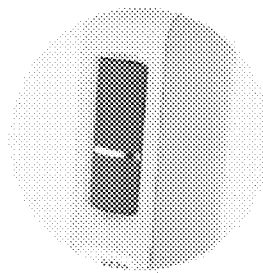
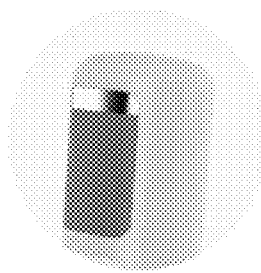

SELECTABLE SINGLE DOSE AUTO-INJECTOR AND METHODS OF MAKING AND USING SAME

CROSS-REFERENCE TO RELATED APPLICATIONS

This is the continuation of U.S. patent application Ser. No. 14/462,116, filed Aug. 18, 2014 claiming priority to provisional U.S. Patent Application No. 61/867,349, filed Aug. 19, 2013, and provisional U.S. Patent Application No. 61/901,721, filed Nov. 8, 2013, which are incorporated by reference herein.

BACKGROUND OF THE INVENTION

Auto-injectors have become very popular and have experienced widespread use due to a variety of advantages that they have over typical manual syringe injectors. Essentially, an auto-injector is an automatic injection system which is designed to subcutaneously deliver a specific dosage of a liquid medicament into an individual.

Disposable auto-injectors are typically single-dose delivery devices used for the periodic injection of a drug. Certain epinephrine-containing auto-injectors are a good example of these types of disposable single dose auto-injectors. One removes the cap, removes a safety, and then rapidly presses one end against their thigh. A needle is either exposed or is advanced by the device into the patient and the injection epinephrine automatically begins. The patient will hold the device in place of a prescribed count and then remove and dispose of the device.

Alternatively, an auto-injector can require the user to remove the cap, press the device against the skin, and press a button for the injection to occur. In both types of auto-injector the device automatically shields the needle before and after injection.

IMITREX®, brand sumatriptan, is sold as an injectable in a normal vial in which a syringe needle is inserted through a septum into the vial and a dose is drawn in through the needle (IMITREX Injection single-dose vial (6 mg/0.5 mL) (NDC 01730449-02)). However, it is also available in a second distinct type of auto-injector. It is sold as part of either an IMITREX STATdose System®, 4 mg kit, (containing 1 IMITREX STATdose Pen, 2 prefilled single-dose syringe cartridges, and 1 carrying case (NDC 0173-0739-00)) or an IMITREX STATdose System®, 6 mg kit, containing 1 IMITREX STATdose Pen, 2 prefilled single-dose syringe cartridges, and 1 carrying case (NDC 0173-0479-00)).

In both of these injector systems, a single dose, pre-measured cartridge, including a needle is loaded into the injector before use and the cartridge is disposed of after use. The injector is reusable. There is no way to select a dose—one either has the 4 mg kit or the 6 mg kit. If some other dose is desired, a traditional syringe and vial must be used.

Existing sumatriptan injection devices deliver, without any ability to change the dose, a single dose of a clear, colorless to pale yellow, sterile, nonpyrogenic solution for subcutaneous injection. Each 0.5 mL of commercial sumatriptan injection solution (4 mg) has a concentration of 8 mg/mL of sumatriptan and thus contains 4 mg of sumatriptan (base) as the succinate salt. Commercial formulations also include 3.8 mg of sodium chloride, USP in water for injection, USP. A higher dose is also available wherein each 0.5 mL of sumatriptan injection solution (6 mg) has a concentration of 12 mg/mL and thus contains 6 mg of sumatriptan (base) as the succinate salt. It also contains 3.5 mg of sodium chloride, USP in water for injection, USP. The pH range of both solutions is approximately 4.2 to 5.3. The osmolality of both injections is 291 mOsmol.

The pen-styled design of a syringe is used to deliver multiple doses of a medicament. These devices require the user to set the amount to be delivered, either once or each time they intend to inject themselves. The device may come with a removable and replaceable needle. The user typically "sticks" themselves like they would with any syringe, and then depress the plunger to actuate deliver of the dose. Each dose can be the same, and can be based on such factors as body mass index, or the dose can be variable and based on, for example, a particular blood sugar level. In either event, the pen injector can repeatedly dispense a full dose each time it is used and it is filled such that it can deliver a plurality of doses.

Patent application EP 0713403A1 describes a syringe for administering a fixed volume of liquid pharmaceutical mixtures and generally also other liquids. The syringe is capable of delivering a single dosed in a select range of medicament dosages by first selecting the desired amount of drug to be administered. To avoid the risk of over-dosing or under-dosing, the dose administered by the syringe is pre-set by a physician, medical practitioner, or patient. After the dose amount is selected the syringe must be inserted into a liquid medicament and the desired amount is drawn into the syringe. At this point the device effectively has a fixed volume that can only be used to administer the pre-set dose of the syringe contents to the patient. The structure of the device makes it difficult for a patient to adjust the syringe dose after it has been set even when the syringe is empty. Once the medicament is in the syringe, it is impossible to change from a higher dose to a lower dose without discharging any medicament.

International Application WO2011/111006 describes an auto-injector that allows the end-user to self-administer first and second doses of a medicament. However, the volume of both the first and the second doses are fixed to a pre-set amount of medicament. The end-user cannot choose or adjust the first dose to be administered by the auto-injector. The user cannot take the entire volume of medicament contained in the injector at one time. Instead, a user must take a first dose, remove the injector from the injection site, rotate a knob to re-arm the device, and then reposition the injector at an injection site to receive a second injection.

Application WO2011/045554 describes an auto-injector for use with a plurality of syringes. Each syringe contains a different dose of fluid to be administered. The auto-injector device is a two part housing adapted to receive one of a plurality of syringes. The housing has a spacer that allows the housing to receive syringes containing different doses and administer those doses. While this auto-injector provides certain flexibility in the volume of doses administered in terms of receiving a range of syringe sizes capable delivering a commensurate range of doses, those doses are fixed in the syringe received by the housing.

Another popular type of injection device is a pen-style device. Such pen-type injection devices may contain a dose metering mechanism that administers a dose based on end-user selection. These devices are portable and may be re-useable or disposable.

Such injection devices that allow the end-user to select the administered dose are described, for example and without limitation, in U.S. Pat. No. 5,938,642 ('642 patent). The '642 patent describes an injection pen device with a dose setting mechanism within the housing that incorporates a dial assembly. The end-user can select a dose by rotating the dial. The device is designed to administer multiple doses of a medicament over an extended period of time. The dose of the medicament to be delivered is not pre-set and can be varied over a wide range of doses. The dose selected by the end-user is based on the titration of a known indicator, such as glucose levels in the blood of the end-user when administering insulin. Based on this information, the end-user dials in the requisite dosage.

Although auto injectors that deliver pre-set or variable doses have been used, there is a need for a single-use, disposable device that provides flexibility in the dose delivered, is user friendly in terms of dose selection, yet more reliable in terms of preventing the administration of incorrect doses.

BRIEF SUMMARY OF THE INVENTION

Described herein is a selectable single dose auto-injector and methods of making and using the same to administer a pharmaceutical composition subcutaneously and wherein the dose is selected by the end-user based on an end-user's perception of symptom severity. For example, an injection device has a dosage indicator and a selection mechanism that permits the user to select a dose from among those the injection device is configured to deliver. If the end-user selects the setting for "less severe" pain or other symptom, the selection will translate to the injection device delivering the lower dose of the pharmaceutical composition. If the end-user selects the setting for "more severe" pain or other symptom, the selection will translate to the injection device delivering the higher dose of the pharmaceutical composition.

One aspect of the disclosure describes a method of treating a headache, cluster headache, or migraine. The method includes choosing a dose amount; actuating a single selectable dose, self-contained, auto-injector; and delivering the selected dose into a patient. The dose can be selected from among a higher dose and a lower dose of an active agent useful for treating a headache, cluster headache, or migraine.

In one embodiment, the auto-injector may contain a predetermined volume of a liquid containing the active agent at a fixed concentration. The auto-injector can be configured to deliver either a single higher or single lower dose, such that it will deliver either substantially the entire volume of liquid containing the active agent to provide the higher dose of the active agent or a lesser volume thereof sufficient to provide the lower dose of the active agent.

In another embodiment, the auto-injector may contain at least a predetermined volume of liquid containing the active agent at a fixed concentration corresponding to a higher dose and deliver only one of a single higher volume corresponding to the higher dose or a single lower volume corresponding to the lower dose.

The method can further comprise rendering the auto-injector unable to deliver any remaining volume of the active agent after delivering either the higher or lower dose.

In another aspect of the disclosure, the end user may select one of the doses based on the perceived severity of symptoms including the patient's experience with the pathology of the patient's condition and reaction to the full and partial doses.

In at least one embodiment, the active agent is a Non-Steroidal Anti-Inflamatory Drug (NSAID) such as aspirin, acetaminophen, ibuprofen or naproxen, a triptan such as, without limitation, sumatriptan, rizatriptan, frovatriptan, zolmitriptan, eletriptan, and naratriptan, or other drug regularly used for treating pain, headache pain in general, or migraine or cluster headaches specifically, or their symptoms. These active agents can be used in the amounts normally associated with their use to treat headaches generally and migraine and cluster headaches specifically.

In one embodiment, actuating the auto-injector can include actuating the auto-injector by manipulating a dial, slide, thumb wheel, pushbutton, or shaking the injector, or by audio selection.

In another embodiment, there is a signal that indicates which one of the two pre-determined doses that the end-user has selected. The signal may be audible, tactile, visual, or any combinations thereof. In a further embodiment, the audible indicator comprises a click, beep, buzzing sound or audible spoken instructions. In a still further embodiment, the tactile indicator comprises a three-dimensional texture on the device. In another embodiment, the visual indicator comprises indicia in the form of color, light, or shape.

The method of treating a pain, migraine, headache, or cluster headaches (or any other condition or affliction mentioned herein) may further include a lower dose of medicament is about 20%, 25%, 30%, 34%, 40%, 50%, 60%, 67%, and 75% of the higher dose. The percent composition of the lower dose may be calculated by weight of the active agent or by volume of the liquid containing the active agent.

Sumatriptan, as used herein, includes all forms of sumatriptan, including free forms, salt forms, etc.

In one embodiment, the active agent is sumatriptan and the higher dose may provide 6 mg of sumatriptan and the lower dose may provide 3 mg or 4 mg of sumatriptan. In one embodiment, the higher dose is 6 mg of sumatriptan as the succinate salt (sumatriptan succinate hereinafter) and the lower dose may provide 3 mg or 4 mg of sumatriptan succinate. In another embodiment, the higher dose may provide 6 mg of sumatriptan succinate and the lower dose may provide 3 mg of sumatriptan succinate.

An alternate embodiment of a method of treating a headache may comprise choosing a preset lower dose of an active agent useful for treating a headache from amongst at least a preset higher and preset lower dose deliverable from a self-contained, auto-injector containing at least sufficient volume of a liquid containing the active agent to provide the higher dose; and auto-injecting the lower dose of the active agent into the patient. Further, the active agent may be a triptan and the preset lower dose being about 34%, 40%, 50%, 60%, or 67% of the higher dose, by weight of the triptan or by volume of the liquid containing the triptan. The triptan can be sumatriptan and the higher dose can be 6 and the lower dose may be 3 or 4 mg of sumatriptan base. In some embodiments, the method comprises no more than two auto-injectors used for a patient in a single 24 hour period.

Still another aspect of the disclosure describes a method of making a self-contained, single selectable dose auto-injector comprising providing a single selectable dose injector capable of being actuated to dispense, once, one of two predetermined volumes of a liquid containing an active agent useful for treating headaches, the two predetermined volumes corresponding to two different doses of the active agent; filling the auto-injector with a sufficient volume of the liquid containing the active agent to provide two different doses to produce a self-contained single selectable dose auto-injector; and packaging the self-contained, single selectable dose auto-injector that is substantially ready for use.

Another aspect of the disclosure describes a single selectable dose, self-contained, auto-injector having a body, a selector, an indicator, a medicament reservoir, a trigger, a needle, and a locking mechanism. The selector can be used to select one of two preset and pre-determined doses. The needle can be disposed with the injector body in a first position and partially extend outside of the injector body in a second position. The needle may be used to inject medicament from the reservoir into a patient when the needle is in the second position. The needle can be moved from the first position to the second position when the trigger is pressed against a user's skin. The locking mechanism can permanently lock the auto-injector after making an injection.

BRIEF DESCRIPTION OF THE DRAWINGS

A more complete appreciation of the subject matter of the present invention and the various advantages thereof can be realized by reference to the following detailed description, in which reference is made to the accompanying drawings:

FIG. 7A-7B shows additional embodiments of the selector of FIG. 6.

DETAILED DESCRIPTION

Figure 1:
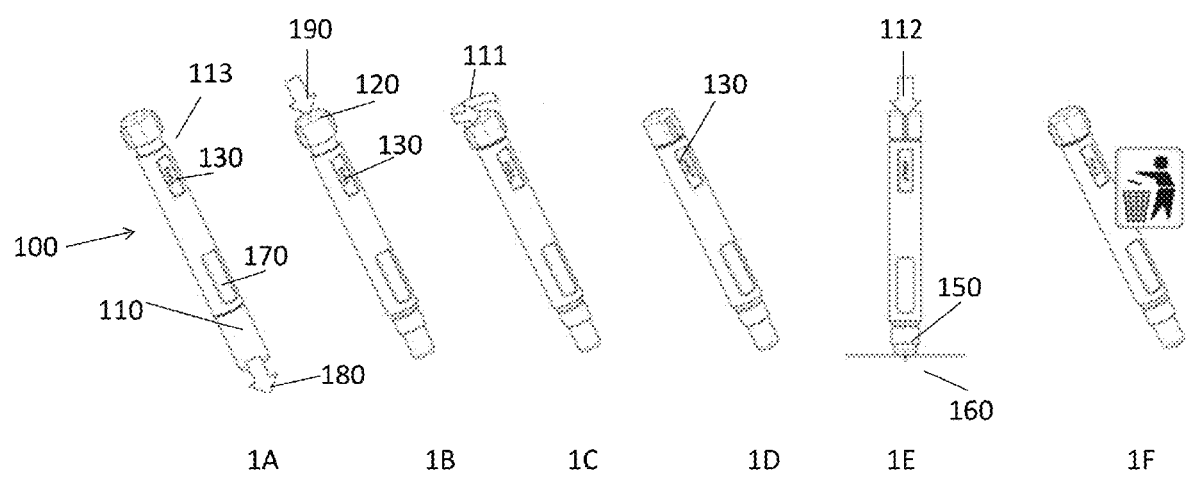
FIG. 1 illustrates a method of using one embodiment of the injection device in accordance with the current invention.

An automatic injection device (also referred to herein as an "auto-injector") for administering a liquid pharmaceutical composition or medicament or drug is described herein. Although some drugs have been specifically listed herein, it is to be understood that this list is in no way meant to be exhaustive. Any injectable drugs suitable for use in the methods and devices described herein are contemplated. Further, drugs identified as their free form include their salt form or other known forms. By way of non-limiting example, sumatriptan as used herein includes sumatriptan as the succinate salt (i.e., sumatriptan succinate), etc.

The terms such as 'about', 'up to', 'generally', 'substantially' and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value.

The auto-injector is a self-contained, single use, preset and prefilled device configured to present a dosing choice to an end-user and to deliver a dose associated with the choice made by the end-user. As such, the auto-injector is configured to be capable of delivering a single dose chosen from a plurality of different doses of a pharmaceutical composition or medicament. In one aspect the auto-injector is configured to be capable of delivering a single dose chosen from two different doses of a pharmaceutical composition or medicament. In other words, the device is capable of delivering different preset doses. The dosing choice is made by the end-user, who then adjusts or actuates the device to deliver the chosen dose, prior to injecting himself/herself with the auto-injector.

The auto-injector is thereby configured to administer to a patient a pharmaceutical composition stored in a medicament reservoir disposed within it. The medicament reservoir cooperates with the dose selection component so that only the volume of pharmaceutical composition, at a given concentration corresponding to the selected dose is administered to the patient using the device. In one other embodiment the medicament reservoir is a cartridge incorporated into the auto-injector housing, either permanently or removably.

In some aspects of the invention, the patient's choice (of the higher and lower doses offered by the device to the end-user is selected) is based on the patient's perceived severity of the patient's symptoms and/or their history and experience with how their body is affected by the pathology of their condition (at various times and circumstances) balanced against possible side effects.

In one aspect, selection of the dose, either the higher dose or some lower, yet already preset dose, is made by some form of manipulation of the injector such as by use of a button, slide, dial, shaking, audible selection, or other input mechanism on the self-contained, single use, auto-injector. The injection device is calibrated so that only the amount of medicament that corresponds to the end-user dosage selection is dispensed from the reservoir and administered to the patient. One type of dose selector contemplated for use in the injector is disclosed in U.S. Pat. No. 5,938,642, the disclosure of which is herein incorporated by reference as if fully set forth herein. Other selectors are also contemplated such as a dial, thumb wheel, slide, switch, etc. In other embodiments, the injector could have a microphone to allow a user to vocally select the desired dose. In still further embodiments, the injector could have an accelerometer to allow a user to change the dosage by shaking, tapping, rotating the injector, etc.

The auto-injector includes an indicator for the user to know which dose, if either, has been selected. Indicia or other ways of indicating either the actual amount selected and/or that the full or a fractional dose is to be given could be included. The embodiments in FIGS. 1-3 include a window or other display indicating whether one has selected the full or half dose (e.g. "Full", "Half", "Partial", "100%", "50%", "0.5 mL", "0.25 mL", "6 mg", "3 mg", "Adult", "Child"). Additionally, the indicia in the information display could say "safe," "lock," or other word to indicate that no dose has been selected. The words or doses could be in different colors, the same colors with different colored backgrounds, could be in different type and or different sizes, or any combination. In other embodiments, the injector can have an indicator arrow which moves when the selector is manipulated to align the arrow with the selectable dose.

The device could also have an LED or LCD screen, such as those found in so called digital thermometers, that indicates the volume of dose when one of the two choices is selected based on information placed on a small chip on the cartridge indicating dose or volume. The device could also have this information programmed into it if it is a self-contained device as described herein or a cartridge accepting device that can only accept one size cartridge. Alternatively, the cartridge could contain a bar code, RFID transponder, or other indicator that is read by the device and the dose indications are changed automatically.

An audio indicator can also be used. For example, a speaker could be incorporated into the auto-injector to provide audio feedback. Further, the speaker could be attached to an integrated circuit capable of providing instructions for using the auto-injector. One integrated circuit contemplated for use in the auto-injector is disclosed in WIPO Publication No. 2012/164402 the disclosure of which is hereby incorporated by reference as if fully set forth herein. Audio instructions can be particularly useful when the person administering the dose to the user is not familiar with operation of the device. Indicators can be configured for the sight impaired (tactile or audio indicators). Indicators can be provided in different or universal languages. An indicator could also provide tactile feedback such as vibration, three dimensional shapes on the injector body, etc.

In a further embodiment of the injection device, the device is capable of offering the end-user a choice between a partial (lower) dose or a full (higher) dose of the pharmaceutical composition. A "full dose" is a "higher dose" defined by a predetermined volume of liquid containing the active agent at a fixed concentration, corresponding to essentially the entire reservoir volume of the device. As noted above, an end-user experiencing less severe symptoms, or expecting to be afflicted with less severe symptoms based on how they feel and past experience, may select the lower or lesser dose. End-users experiencing, or expecting to experience, more severe symptoms will select the higher dose. In some devices in accordance with the invention, this higher dose is a full dose and represents substantially all of the liquid volume held in the auto-injector. In other instances, the auto-injector may have substantially more active agent-containing liquid in its reservoir than needed to provide a relatively higher dose—the highest dose that the auto-injector is set to provide. By way of example, and not by way of limitation, the device is capable of offering the end-user a choice of 6 mg of sumatriptan as the higher dose and 3 mg of sumatriptan as the lower dose. In one embodiment, sumatriptan is in the form of sumatriptan succinate.

In one embodiment, the single use, self-contained auto-injector can be pre-loaded with a volume of liquid solution containing the active agent corresponding to the higher dose. The higher dose amount can range from 3-12 mg of active agent and the volume injected ranges from 0.1 to 2 mLs. The pre-selected and preset lower dose is about 20%, 25%, 30%, 34%, 40%, 50%, 60%, 67% or 75% of the full or maximum dose by weight of the active agent or by volume of the liquid containing the active agent. This allows the self-contained, single use auto-injector to be set to deliver 100% of the dose or a single dose of any percentage less than 100% as the only other option (e.g. 25% or 100%; 33% or 100%; 60% or 100%; 67% or 100%; 75% or 100%). Any time that either the full dose, or the lower dose (lower volume) is selected and delivered, the remainder of the original dose and volume, if any, are disposed of with the single use device. And these doses, (the full dose or higher dose and the lower dose) are preset. By preset, it is meant that while the patient or operator may select between a full or higher dose and a lower or lesser dose, they cannot merely select any higher and/or any lower dose—both are predetermined and the device will only provide those preset doses. To use a different higher or lower dose would require a different auto-injector preset for those doses.

In one embodiment for treating migraines, the higher dose amount is 6 mg of sumatriptan and the lower dose amount is 3 mg or 4 mg of sumatriptan. In one aspect of the above embodiment, the lower dose amount is 3 mg of sumatriptan.

Accordingly, in one embodiment, a patient suffering from a headache, and in particular a migraine or cluster headache is treated using a device in accordance with the invention which is a self-contained, single dose auto-injector which can provide either a preset higher or a preset lower dose as previously described. Such patients are very familiar with the unique pathology of their condition. They tend to be aware of their triggers, how their surrounding will impact the duration, severity and symptomology of each attack. They also tend to understand the way in which the medications that they take can impact the pathology of that attack and how they can be impacted by the side effects of that medication. Sumatriptan, for example, is a medication within the drug class selective serotonin receptor (5HT) agonists and is available as a generic drug and is used in oral, intranasal or injectable dosage forms. Common side effects of sumatriptan are pain or chest tightness, weakness and stomach discomfort.

Patients are in a unique position to self-medicate for these limited conditions, within the safe limits offered by these self-contained, single use, auto-injectors. These auto-injectors are prescribed specifically so that a treating healthcare provider can be involved in the dosing decisions. By selecting the injector, the size of the full dose, and the degree of the lower dose, the health care provider can prevent under-dosing that would be ineffective, or overdosing. They can be sure that the patient can, even in severe attacks, be able to provide themselves with a dose that is likely to be effective without having to calculate and manipulate current multi-dose devices like insulin pens. Thus, in accordance with the invention, a patient suffering from a headache, and in particular a migraine or cluster headache, is treated using a device useful in accordance with the invention which can provide a higher or lower dose as previously described.

Ailments that might require self-medication based on a patients knowledge of their own pathology and reaction to various doses of an active agent include, but are not limited to: acute pain; back spasms; fever; cluster headaches; tension headaches; migraine headaches (a term used herein to include treatment of the aura and/or nausea often suffered by migraine sufferers, with our without specific migraine headache pain); asthma; anaphylaxis; irritable bowel disease; multiple sclerosis; Parkinson's disease; and epilepsy.

The injection device of the present invention may contain various active agents (synonymously used herein with medicaments, actives, active pharmaceutical ingredients and drugs) in its reservoir. These include, but are not limited to, the following types of medicaments: analgesics; non-steroidal anti-inflammatory drugs; COX-2 inhibitors; opiods; corticosteroids; triptans; immunomodulatory drugs; catecholamines; dopamine agonists; anticholinergic medications; anticonvulsants; and antiepileptic drugs.

Specific examples of medicaments or pharmaceutical compositions administered by the injection device described herein include, but are not limited to, the following: ibuprofen; aspirin; diclofenac; oxycodone; duloxetine; sumatriptan; rizatriptan; frovatriptan; zolmitriptan; naratriptan; eletriptan; morphine; epinephrine; teriflunomide; interferon beta-1a; interferon beta-1b; glatiramer acetate; fingolimod; mitoxantrone; dimethyl fumarate; natalizumab; Levodopa (L-dopa); carbidopa pramipexole; ropinirole; bromocriptine; selegiline; rasagiline; amantadine; entacapon; memantine; rivastigmine; galantamine; gabapentin; fludrocortisone; Hydrocortisone; hydrocortisone acetate; cortisone acetate; tixocortol pivalate; prednisolone; methylprednisolone; prednisone; triamcinolone acetonide; triamcinolone alcohol; mometasone; amcinonide; budesonide; desonide;

fluocinonide; fluocinolone acetonide; halcinonide; Betamethasone; betamethasone sodium phosphate; dexamethasone; dexamethasone sodium phosphate; fluocortolone; Hydrocortisone-17-butyrate; hydrocortisone-17-aceponate; hydrocortisone-17-buteprate; and prednicarbate, acetaminophen, naproxen, propionic acid drugs such as fenoprofen, flurbiprofen, suprofen, benoxaprofen, ketoprofen, oxaprozin or the like; acetic acid drug such as etodolac, indomethacin, ketorolac, alclofenac, ibufenac, sulindac, clindanac, fenclorac, indoprofen, fenclofenac, pirprofen, benoxaprofen, carprofen or cicloprofen, indomethacin, oxmetacin, acemetazin, cinmetacin, zomepirac, tolmetin, clopirac or tiaprofenic acid or the like; ketone drugs such as nabumetone, sulindac, tolmetin or the like; fenamate drugs such as meclofenamate, mefenamic acid, or the like; oxicam drugs such piroxicam, droxicam, meloxicam, tenoxicam or the like; salicylic acid drugs such as diflunisal, salsalate or the like; pyrazolin acid drugs such as oxyphenbutazone, phenylbutazone or the like; COX-2 inhibitors such as celecoxib, parecoxib, valdecoxib, etoricoxib, rofecoxib, deracoxib, parecoxib or the like; napthylalkanones such as nabumetone; atypical opioid analgesic such as tramadol; opioids such as morphine; ergots such as dihydroergotamine; local anesthetic such as lidocaine; or mixtures or combinations thereof. All the actives, defined above, include all forms of the respective actives such as free forms, salt forms, polymorphs, etc. For example, sumatriptan, as used in this application, includes all forms of sumatriptan, including free forms, salt forms, etc.

In one specific embodiment of the devices and methods of the invention, the medicament to be administered is a triptan. As previously indicated, the medicament to be administered can be one of sumatriptan, rizatriptan, frovatriptan, zolmitriptan, naratriptan, and eletriptan.

In another embodiment of the device, the medicament to be administered is sumatriptan. In this embodiment, the higher dose is 6 mg and a lower dose is 3 mg. In one aspect of the above embodiment, sumatriptan is in the form of sumatriptan succinate.

In another embodiment of the device, the medicament to be administered is epinephrine. In a further embodiment, the device is capable of offering the end-user a choice to select delivery of an adult dose (0.1 to 0.5 mg) or a pediatric dose (0.1 to 0.3 mg) of epinephrine. An adult auto injector allowing for two or more preset doses between 0.1 and 0.5 mg, or a pediatric injector allowing for two or more preset doses between 0.1 and 0.3 mg are also contemplated.

In a further embodiment, the injection device has a lockout mechanism that permanently disables the device from delivering a subsequent dose after the injection device is used to administer the first dose, regardless of whether the first dose was a full or partial dose. For example, the device could have a frangible connection between a primer and actuator such that once the device is used the primer can no longer engage the device to enter the armed state.

A further embodiment has a lockout mechanism that permanently disables the device from delivering subsequent doses only after the entire contents of the reservoir have been discharged by the injection device. In other words, if the lower dose is chosen as the first dose, the device remains capable of delivering the remaining portion of the full dose as a second, subsequent dose before the lockout mechanism deploys and disables the device.

In another embodiment, the injection device is capable of accurately administering a partial or full dose of a medicament or pharmaceutical composition, without having to prime the device prior to administration but may still be configured to be locked after administering a first dose regardless of whether it was a full or partial dose.

In another aspect, the auto-injector is not self-contained and is a multiple use device which can accommodate a single use cartridge. However, the auto-injector will dispense, at the election of the patient, either the full dose or lower dose as previously described. Any time that the lower dose (lower volume) is selected and delivered, the remainder of the original dose and volume are disposed of with the single use cartridge. This auto-injector could be designed to deliver, for example, only 100% or 50% of a specified volume. Alternatively it could be designed to dispense 50% or 100% of the volume contained in the cartridge—where the cartridge volume can vary.

The patient suffering from a headache including cluster headaches and migraine headaches can select a full or higher dose or partial, lower or lesser dose to meet their need from a single dose, self-contained auto-injector of the invention containing a single higher dose of a triptan as discussed herein. They can then inject themselves (or someone else can inject them) with that selected dose and dispose of the injector. Their treatment can also be accompanied by the concomitant administration of a second medication regularly used for treating headache pain in general, or migraine or cluster headaches specifically, or their symptoms. "Concomitantly" as used herein means in coordination with. The doses may be given together, moments or hours apart and may be given by the same or different routes of administration. In a further embodiment, this second medication is administered orally. In still another embodiment, the second medication is an oral NSAID given in the doses normally associated with their use for headache pain.

The self-contained, single selectable dose auto-injector herein described can be manufactured by providing a single selectable dose injector which has a selector. The selector can be actuated to dispense a single time, one of two pre-determined volumes of a liquid containing an active agent useful for treating headaches. As previously described, the two volumes correspond to two different doses of the active agent. The auto-injector is filled with a sufficient volume of the liquid containing the active agent to provide the two predetermined doses to produce a self-contained auto-injector. The injector is packaged in a state that is substantially ready for use.

With reference to the FIG. 1, an auto-injector 100, is provided with a cap 110. The cap 110 is removed in step 1A by moving the cap 110 in the direction indicated by arrow 180. The auto-injector 100 includes a window 170 to indicate whether the device has been used. For example, the window could display one color prior to use and another color after use. As previously described, the window could also display text or symbols to indicate whether the device is ready for use or has been used.

The injector 100 has a button 120 at the injector proximal end 113. As shown, the button 120 performs multiple functions. The button 120 is a priming mechanism to arm the injector 100. The button 120 can also be rotated to select the desired dose. In step 1B, the auto-injector 100 is primed by manipulating button 120 in the direction indicated by arrow 190. In step 1C, the end-user grips the button 120 and rotates in the direction indicated by arrow 111 if the half dose is desired instead of the default full dose. No such rotation is necessary if the full dose is desired. Such doses described herein are exemplary and not by way of limitation. Doses can be configured to be either a full dose or a partial dose as previously discussed.

A display 130 is provided to indicate what dose will be delivered by the device. Such indicators described herein are exemplary and not by way of limitation. In step 1D, the end-user checks the dose selection. In step 1E, the dose is delivered after the user pushes the distal end 150 against the patient's skin 160 in the direction indicated by arrow 112. In step 1F, the auto-injector is discarded properly such as in a "sharps" container.

Figure 2:
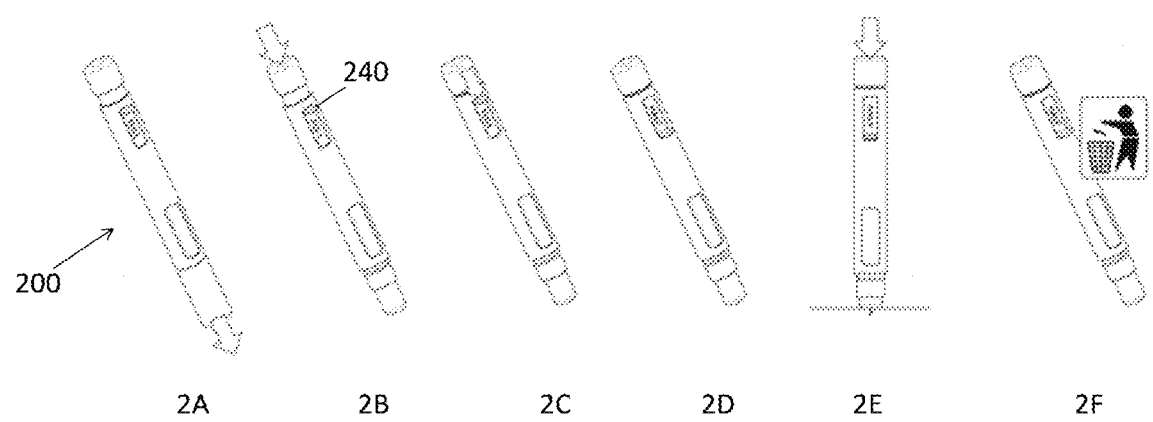
FIG. 2 illustrates a method of using another embodiment of the injection device in accordance with the current invention.

With reference to FIG. 2, the auto-injector 200 is similar to that of FIG. 1. However, the selector shown is a slider 240. Here, a user manipulates the slider 240 to select the dose to be administered. The slider 240 can have indicia to show which dose is being selected. Once the dose is selected, the device can be used in accordance with the description of the embodiment in FIG. 1.

Figure 3:
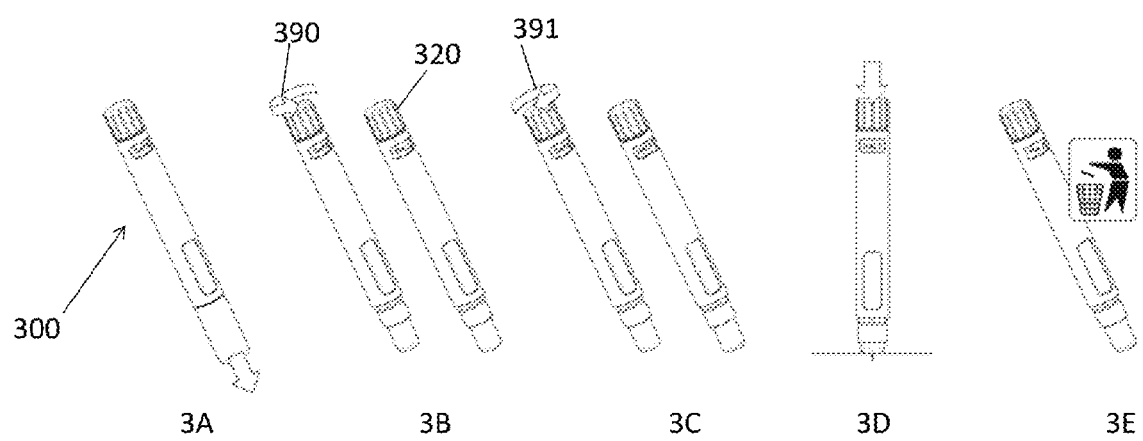
FIG. 3 illustrates a method of using another embodiment of the injection device in accordance with the current invention.
Figure 4:
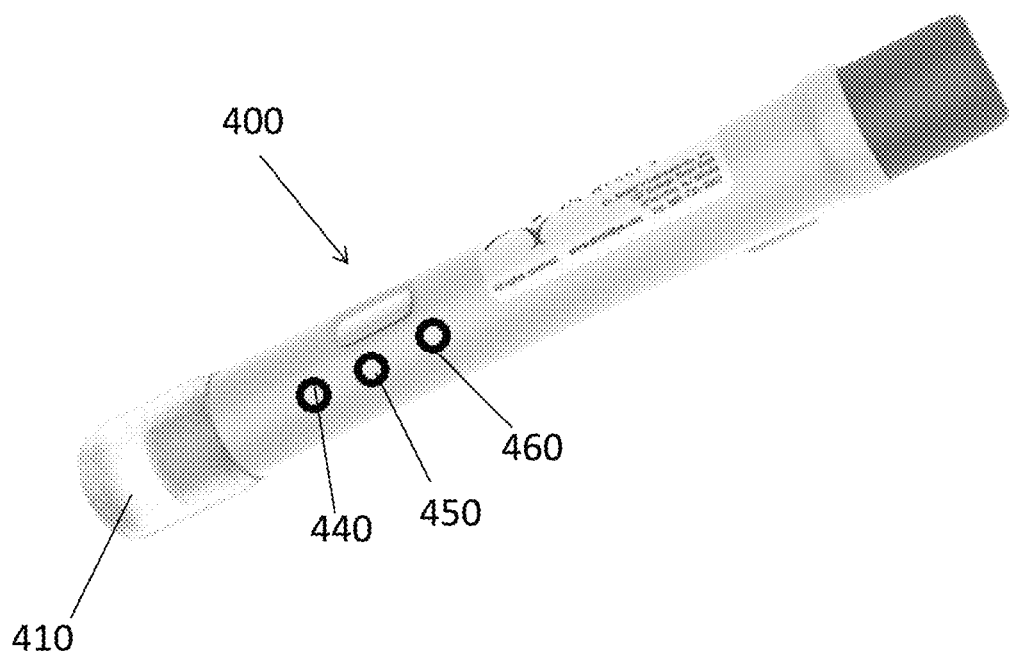
FIG. 4 illustrates an embodiment of the injection device in accordance with the current invention.

The auto-injector 300 of FIG. 3 is an embodiment similar to that of FIG. 1 but has a different method of operating the button 320. In step 3B, the end-user grips the button 320 and rotates it counter-clockwise (390) to unlock the device and select a full dose. In step 3C, the end-user can grip the button 320, and rotate it clockwise (391) to unlock the device and select a partial dose if desired. FIG. 4 shows one embodiment of an auto-injector in accordance with the current invention. The embodiment shown is similar to those previously described but has LEDs 440, 450, 460 positioned on the body 480 of the injector 400 to indicate the dose selected. For example, LED 450 could be illuminated when the cap 410 is removed to indicate the injector 400 is in the "locked" state. LED 440 could be illuminated when the full dose is selected. LED 460 could be illuminated when a partial dose is selected. Of course, any of the LEDs could indicate the status of the auto-injector selection. In addition, LEDs could be used to reflect whether the device has been used.

The injector body can also incorporate anti-roll features. For example, the body could have a cross sectional shape other than circular (e.g. triangle, trapezoid, square, oval, etc.). The body could also have one or more bumps formed on it to prevent rolling. The body cross-sectional diameter could be greater at one end than the other to reduce the likelihood of rolling when the indicator is placed on a surface.

Figure 5A:
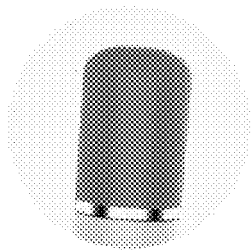
FIGS. 5A-5D show several embodiments of the selector of FIG. 4.
Figure 5B:
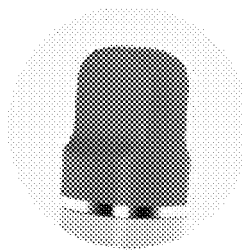
Figure 5C:
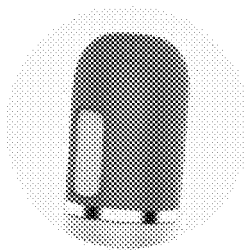
Figure 5D:
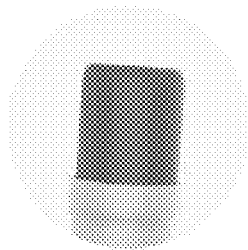

FIGS. 5A-5D show several embodiments of a selector in accordance with the current invention. The selectors could be incorporated, for example, into the injector shown in FIG. 4. FIG. 5A provides a circular selector. The selector shown in 5B has flat sides to improve the grip to rotate the selector. The selector shown in 5C has rubber inserts to improve the grip on the selector. The selector shown in 5F has a circular shape similar to 5A, but the selector in 5D has a more squared off upper edge.

Figure 6:
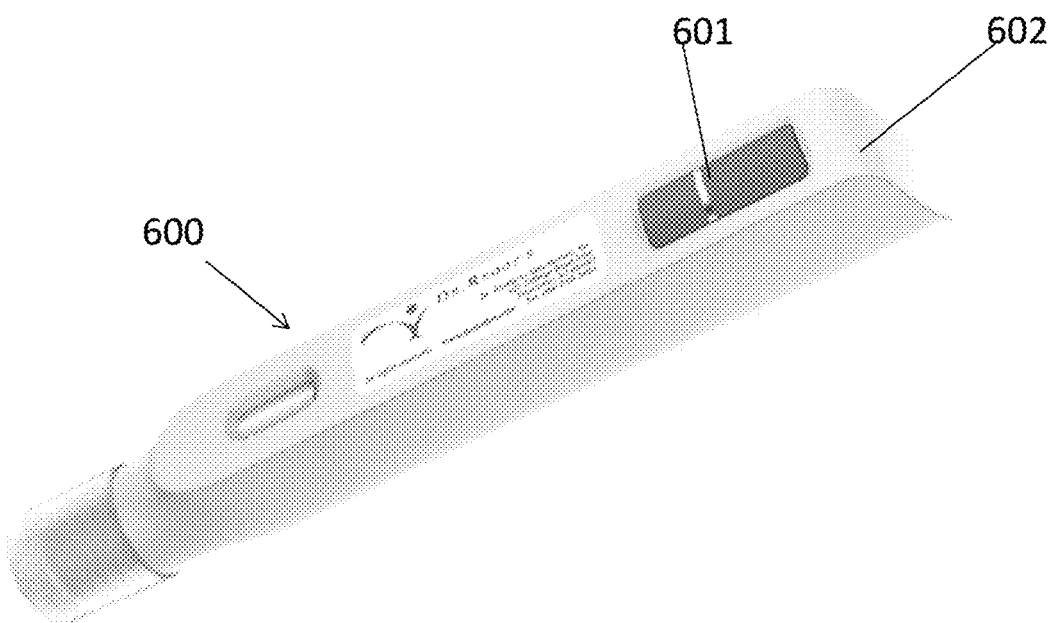
FIG. 6 shows an embodiment of the injection device in accordance with the current invention.

FIG. 6 shows an embodiment of the auto-injector in accordance with the current invention. The auto-injector 600 includes a protected dial 601. The injector 600 does not incorporate a primer but instead is in a continual ready for use state. The end of the dial 601 is protected by a covering 602. The covering 602 prevents accidental manipulation of the dial 601 when a patient is preparing to, or in the process of, using the injector 600.

FIGS. 7A and 7B shows further embodiments of a selector in accordance with the current invention which can be incorporated into the embodiment shown in FIG. 6. The selector can be incorporated as described, for example, in FIG. 1. FIG. 7A shows a slider selector and 7B shows a rotating selector.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a headache in a patient comprising:
   providing a single auto-injector, the auto-injector comprising a body, a selector, and a medicament reservoir;
   selecting a single dose from the group consisting of a higher dose of 6 mg or a lower dose of about 3 mg of sumatriptan using the selector, wherein the medicament reservoir contains 6 mg of the sumatriptan and the single auto-injector is configured to deliver only the higher dose or the lower dose of the sumatriptan; and
   auto-injecting the selected single dose of the sumatriptan from the single auto-injector into the patient, wherein the higher dose is selected based on more severe symptoms or pain and the lower dose is selected based on less severe symptoms or pain.

2. The method of claim 1 wherein the selection of a single dose is accomplished by manipulating a dial, slide, thumb wheel, pushbutton, or toggle switch of the auto-injector.

3. The method of claim 1 wherein the selected single dose is indicated by indicia, a tactile indicator, audible indicator or any combination thereof.

4. The method of claim 1 wherein the headache is selected from the group consisting of migraine or cluster headache.

5. The method of claim 1 wherein the sumatriptan is in the form of sumatriptan succinate.

6. The method of claim 1, wherein no more than two auto-injectors are used for the patient in a 24 hour period.

7. The method of claim 1, wherein the selecting is accomplished by manipulating a dial, slide, thumb wheel, pushbutton, or toggle switch of the auto-injector, and the selected single dose is indicated by indicia, a tactile indicator, audible indicator or any combination thereof.

8. A method of treating a headache in a patient comprising:
   providing a single auto-injector, the auto-injector comprising a body, a selector, and a medicament reservoir;
   selecting a single dose from the group consisting of a higher dose of 6 mg or a lower dose of about 4 mg of sumatriptan using the selector, wherein the medicament reservoir contains 6 mg of the sumatriptan and the single auto-injector is configured to deliver only the higher dose or the lower dose of the sumatriptan; and
   auto-injecting the selected single dose of the sumatriptan from the single auto-injector into the patient, wherein the higher dose is selected based on more severe symptoms or pain and the lower dose is selected based on less severe symptoms or pain.

9. The method of claim 8 wherein the selection of a single dose is accomplished by manipulating a dial, slide, thumb wheel, pushbutton, or toggle switch of the auto-injector.

10. The method of claim 8 wherein the selected single dose is indicated by indicia, a tactile indicator, audible indicator, or any combination thereof.

11. The method of claim 8 wherein the headache is selected from the group consisting of migraine and cluster headache.

12. The method of claim 8 wherein the sumatriptan is in the form of sumatriptan succinate.

13. The method of claim 8 wherein no more than two auto-injectors are used for the patient in a 24 hour period.

14. The method of claim 8, wherein the selecting is accomplished by manipulating a dial, slide, thumb wheel, pushbutton, or toggle switch of the auto-injector, and the selected single dose is indicated by indicia, a tactile indicator, audible indicator or any combination thereof.

* * * * *